United States Patent [19]
Imran

[11] Patent Number: 5,853,419
[45] Date of Patent: Dec. 29, 1998

[54] STENT

[75] Inventor: Mir A. Imran, Los Altos Hills, Calif.

[73] Assignee: Surface Genesis, Inc., Menlo Park, Calif.

[21] Appl. No.: 818,274

[22] Filed: Mar. 17, 1997

[51] Int. Cl.$^6$ .............................. A61M 29/00; A61F 2/06
[52] U.S. Cl. ................. 606/191; 606/198; 623/1
[58] Field of Search .................... 606/1, 190–200; 604/96; 623/1, 11, 12

[56] References Cited

U.S. PATENT DOCUMENTS

| | | | |
|---|---|---|---|
| 5,449,373 | 9/1995 | Pinchasik et al. | 606/198 |
| 5,591,197 | 1/1997 | Orth et al. | 606/194 |
| 5,643,339 | 7/1997 | Kavteladze et al. | 606/194 |
| 5,702,419 | 12/1997 | Berry et al. | 606/108 |

*Primary Examiner*—Glenn K. Dawson
*Attorney, Agent, or Firm*—Flehr Hohbach Test Albritton & Herbert LLP

[57] ABSTRACT

A stent including a cylindrical member having an outside diameter, a length and having proximal and distal extremities. The stent is formed of a metal and has a wall defining a central bore having a longitudinal axis extending from the proximal extremity to the distal extremity. The cylindrical member has at least two longitudinally spaced-apart struts extending in the wall and permit radial expansion of the cylindrical member from a contracted condition to an expanded condition. Ribs extending in the wall prevent shrinkage in length of the cylindrical member as it is expanded from a contracted position to an expanded position.

2 Claims, 1 Drawing Sheet

STENT

BACKGROUND OF THE INVENTION

This invention relates to a stent and more particularly to a stent for placement in a vessel in a living body.

Stents have heretofore been provided. However, they had the disadvantage that when they are expanded, they shrink in length. This shrinkage in length has created a number of problems. For example it has been found that this shrinkage may cause damage to the balloon which is utilized for expanding the stent. In addition because of such shrinkage, it has been difficult for the physician deploying the stent to precisely position the stent in the vessel. Such shrinkage has often been as much as 25–35% of the length. There is therefore a need for a new and improved stent which overcomes these difficulties.

In general, it is an object of the present invention to provide a stent which can be expanded without shrinking in length.

Another object of the invention is to provide a stent of the above character which can be physically expanded by the use of a balloon or alternatively which can be formed so that it will be self-expanding.

Another object of the invention is to provide a stent of the above character which can be provided in various lengths while still retaining flexibility.

Another object of the invention is to provide a stent of the above character in which one or more ends of the stent can be flared.

Additional objects and features of the invention will appear from the following description in which the preferred embodiments are set forth in detail in conjunction with the accompanying drawings.

DETAILED DESCRIPTION OF THE PREFERRED EMBODIMENTS

In general, the stent of the present invention comprises a cylindrical member having an outer diameter, a length and proximal and distal extremities. It is formed of a metal and has a wall defining a central bore having an axis and extending from the proximal extremity to the distal extremity. The cylindrical member has at least two spaced-apart struts which are spaced apart longitudinally of the axis which permit radial expansion of the cylindrical member. Means is provided extending in the wall to prevent a decrease or shrinkage in length of the cylindrical member as the cylindrical member is expanded radially from a contracted position to an expanded condition.

Figure 1:
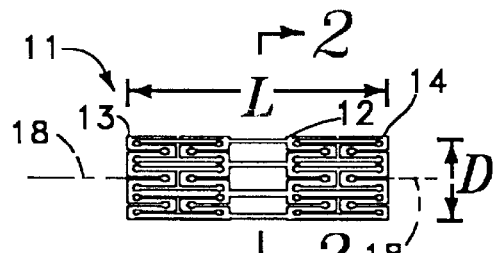
FIG. 1 is an enlarged side elevational view of a stent incorporating the present invention.
Figure 2:
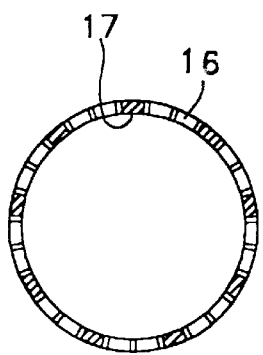
FIG. 2 is a cross-sectional view taken along the line 2—2 of FIG. 1.
Figure 3:
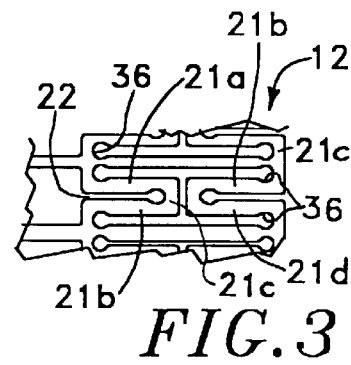
FIG. 3 is a still further enlarged portion of the stent shown in FIGS. 1 and 2.

More particularly as shown in FIGS. 1, 2 and 3 of the drawing, the stent 11 is comprised of a cylindrical member 12 which has an outside diameter represented by the dimension "D" and a length represented by the diameter "L" in FIG. 1. The cylindrical member 12 has proximal and distal or first and second extremities 13 and 14. The cylindrical member 12 is formed of a suitable metal such as a stainless steel 316 for implantation in the human body. Alternatively, it can be formed of a shape memory material such as a Nitinol to provide self-expanding characteristics as hereinafter described.

The cylindrical member 12 has a wall 16 which defines a central bore 17 having a central longitudinal axis 18 and extending from the proximal extremity 13 to the distal extremity 14. By way of example, the outside diameter D can be 0.055" but can range from 0.010" to 0.130". The thickness of the wall 16 for example can be 0.005" but can range from 0.001" to 0.02".

Figure 4:
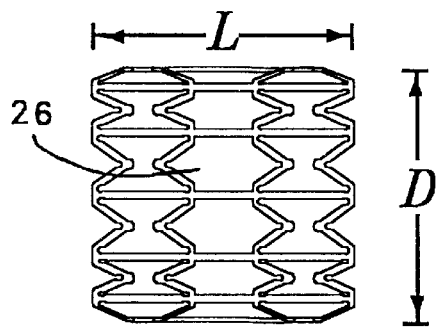
FIG. 4 is a side elevational view of the stent shown in FIG. 1 in an expanded position showing that it does not decrease in length or shrink in length as the stent is expanded.

Means is provided in the wall 16 permitting radial expansion of the cylindrical member from a contracted position to an expanded position and consists of a plurality of at least two and preferably more struts 21 which are spaced apart longitudinally of the axis 18. Each of the struts has at least two portions as for example portions 21a and 21b as shown in FIG. 1 which are folded or overlap each other in the wall 16 in a direction which at least extends partially along the axis 18. Thus, as shown in FIG. 1, the portions 21a and 21b lie substantially parallel to each other and substantially parallel to the axis 18 and are adjoined by a portion 21c having a slot 22 extending therebetween and opening in a region which is remote from the portion 21c. Thus the portions 21a and 21b can be characterized as first and second legs which are adjoined at one end and which have their other ends secured to and forming a part of the wall 16. The struts 21 are circumferentially disposed about the circumference of the wall 16. In accordance with the present invention, at least three of such struts 21 preferably five or more are provided preferably equally spaced around the circumference. Two or more closely approximate a circle. Thus as shown in FIGS. 1 and 4, eight of such struts are provided around the circumference. The struts 21 are arranged so that the slots 22 between the portions 21a and 21b open into the proximal and distal extremities 13 and 14. As can be seen in FIG. 1, the slots 22 open through the ends or proximal and distal extremities 13 and 14 of the cylindrical member 12. Additional struts 21 can be oriented in the same directions as the two outermost struts 21. The slots 22 facing each other at opposite sides of the mid-point of the cylindrical member 12 form a part of a hexagon-like cell 26 as hereinafter described.

Means is provided extending in the wall to prevent a decrease or shrinkage in length of the cylindrical member 12 as it is expanded from the contracted position and is comprised of a plurality of circumferentially spaced apart ribs 31 preferably equally spaced about the circumference of the cylindrical member 12 and which extend between the proximal and distal extremities 13 and 14 in directions which are substantially parallel to the longitudinal axis 18. At least three of such ribs 31 are provided. However, as pointed out previously, it is desirable in order to more closely approximate a circle that five or more ribs as for example nine ribs as shown be provided. As shown in FIGS. 1 and 2, the struts 21 extend between the ribs 31. Thus for example one set of struts extends between each two adjacent ribs to provide the cylindrical member 12. With the construction shown in FIGS. 1 and 2 it can be seen that ribs 31 extend from one end to the other of the cylindrical member 12 as shown in FIG. 1 and that the struts 21 are all bracketed by the ribs 31.

From the foregoing it can be seen that the ribs 31 form two of the hexagonal sides of the cell 26. The struts 21 each having two portions 21a and 21b form the additional four sides of the hexagonal cell. The use of a hexagonal cell is desirable because it provides radial strength and compression resistance. Thus in each stent it is desirable to have at least one hexagonal cell 26 to provide additional strength to the cylindrical member 12 forming the stent. The struts 21 should have a cross-sectional area of less than approximately one-half of that of the cross-sectional area of the ribs 31 so that the struts 21 will not deform the ribs 31 when the cylindrical member 12 is expanded. The stent which is shown in FIGS. 1 and 2 should have a length which is at least as great as the diameter in the expanded position to inhibit rolling over of the stent during use. Thus, a length of 3–4 mm is desirable.

The foregoing construction of the cylindrical member 12 to provide a stent can be readily accomplished. For example a material formed in the form of a tube can be utilized representing the appropriate contracted outside diameter and having the appropriate wall thickness. It can have the desired pattern as hereinbefore described formed therein by the use of conventional etching or laser cutting techniques. When this is done, the struts 21 and the ribs 31 which remain after the undesired material has been removed form an integral structure in which the ribs 31 and the struts 21 are formed integrally and of the same material. In order to facilitate bending of the struts 21 as hereinafter described in moving from the contracted position shown in FIGS. 1 and 2 to an expanded position as shown in FIG. 4, rounded notches 36 (see FIG. 3) are formed adjacent the junction of the portions 21a and 21b of the struts 21 to the ribs 31 and at the portion 21c. As can be seen, these notches 36 provide a narrowing to provide hinge points to facilitate bending of the struts 21 when the cylindrical member is expanded from a contracted position to an expanded position as shown in FIG. 4.

As can be seen from FIG. 4, the cylindrical member 12 forming the stent 11 can be expanded radially either by self-expansion or by mechanical expansion such as by use of an inflatable balloon. The radial expansion occurs without any shrinking or decrease in length. This lack of shrinkage is indicated by comparing FIGS. 1 and 2 in which the dimension "L" between the contracted position shown in FIG. 1 and the expanded position shown in FIG. 4 remains substantially unchanged. The ribs 31 serve as compression resisting elements preventing shrinkage of the stent in length during movement between contracted and expanded positions. Thus, the ribs 31 form compression resisting elements while still providing good flexibility along the longitudinal axis of the stent. This lack of shrinkage of the stent from movement between the contracted to the expanded positions is advantageous in that there is no sliding movement relative to the balloon if a balloon is used for expanding the stent which could possibly rupture or tear the balloon. In addition since there is no shrinkage, it is much easier for the physician to position the stent in an appropriate location and to ensure that after the stent has been expanded it is still in the selected position.

The stent 11 of the present invention can be deployed in a conventional manner into the desired location. For example it can be deployed using a balloon catheter to carry the stent to the desired site and thereafter inflating the balloon to expand the stent into the desired size after which the balloon can be deflated and removed. Similarly if the stent is formed of a self-expanding material, the stent can be deployed by use of an appropriate stent deployment catheter after which the self-expanding stent can be released to expand to the maximum desired diameter after which the stent deployment catheter can be removed.

Figure 5:
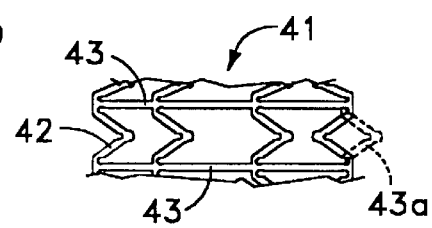
FIG. 5 is a side elevational view of another embodiment of a stent incorporating the present invention.

Another embodiment of a stent incorporating the present invention is show in the stent 41 in FIG. 5. The stent 41 is provided with a plurality of longitudinally spaced apart struts 42 spaced apart longitudinally of the axis 18 and which adjoin longitudinally extending circumferentially spaced apart ribs 43. As shown, the struts 42 are compressed in such a manner so that they always stay within the inner and outer confines of the stent 41. The last strut 42 on the right as viewed in FIG. 5 is reversed in direction and extends inwardly so that nothing protrudes beyond the ends of the stent 41. However, it should be appreciated that if such projection is undesirable and some minimal amount of shrinkage can be accommodated, the strut 42a to the right as shown in dotted lines can continue to face in the same direction as the other struts 42. The manufacture and operation and use of the stent 41 in other respects is identical to that hereinbefore described with respect to the previous embodiment of the invention.

Figure 6:
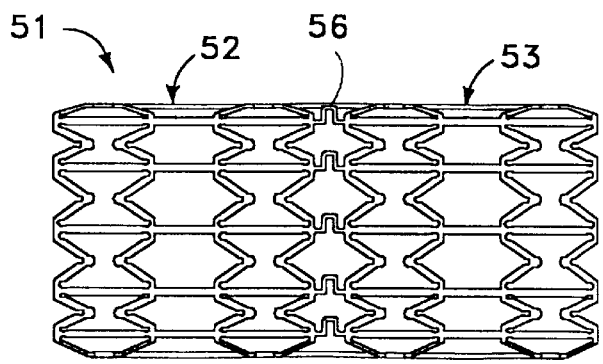
FIG. 6 is a side elevational view of a stent of greater length incorporating the present invention.

When it is desired to have a longer stent than is typical, a construction such as shown in FIG. 6 can be utilized in which a plurality of interconnected stent portions are provided. Such a stent 51 is shown in FIG. 6 and as shown therein consists of first and second stent portions or segments 52 and 53 which can have construction which is substantially identical to the construction shown in FIGS. 1 through 4. These segments 52 and 53 which can be of a suitable length as for example 3–4 mm are interconnected to form a unitary construction while still retaining flexibility by providing U-shaped links 56 which can be formed integral with the segments 52 and 53 and of the same material by laser machining or etching in the manner hereinbefore described. As can be seen, these links 56 have a smaller cross-sectional area than the ribs 31 to provide improved flexibility between the segments 52 and 53 so that curvatures in the vessel in which the stent 51 is being placed can be readily accommodated. Although only two segments have been provided, it should be appreciated that additional segments can be arranged in tandem and interconnected in the same manner to provide a stent of any desired length while still retaining the desired flexibility in accommodating bends in vessels. Such a stent can be deployed in a conventional manner. For example, it can be expanded by use of a balloon or balloons or alternatively can be formed of a self-expanding material.

Figure 7:
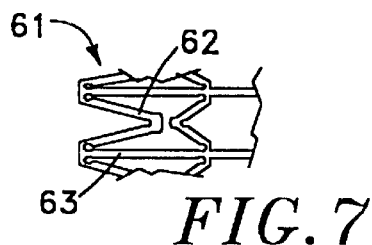
FIG. 7 is a side elevational view of another embodiment of a stent incorporating the present invention in which one end of the stent can be flared to a greater diameter than the remainder of the stent.
Figure 8:
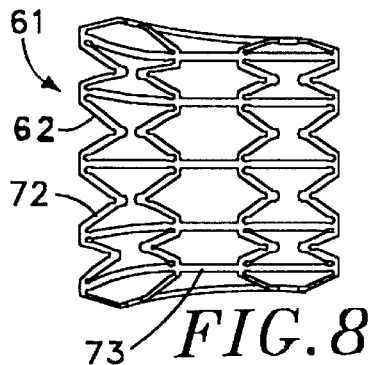
FIG. 8 is a side elevational view showing a stent which has been expanded in which one end is flared.
Figure 9:
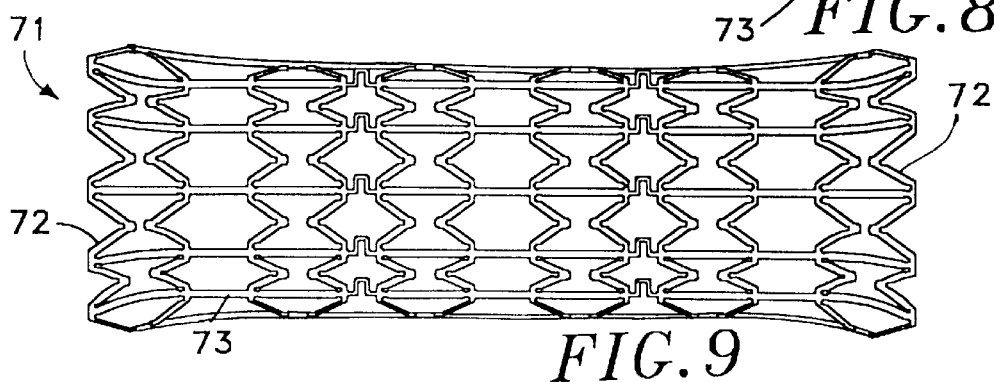
FIG. 9 is a side elevational view showing a stent incorporating the present invention in which both ends have been flared.

Another embodiment of the invention is shown in FIG. 7 which shows a portion of a stent 61 having struts 62 spaced apart longitudinally of the axis of the stent and adjoining longitudinally extending circumferentially spaced apart ribs 63. The struts 62 rather than being of all of the same length as in the previous embodiments hereinbefore described have differing lengths. Thus as shown in FIG. 7, the strut 62 immediately adjacent the left end of the stent 61 as shown in FIG. 7 is longer than the other struts. This makes it possible when the stent 61 is expanded as shown in FIG. 8 to have one end, the end adjacent the longer strut 62 to be flared outwardly as shown and to taper inwardly gradually to a smaller diameter. This flaring on one end may be desirable in certain applications in which it is desirable that the stent more securely grasp the vessel, as for example a carotid artery, in which it is disposed to prevent longitudinal movement of the stent after the stent has been deployed. This additional expansion at one end can be readily achieved merely by expansion of the balloon used for expanding the stent. Similarly, if it is desired to have flared ends at both ends of the stent as shown in FIG. 9, this can be readily accommodated by providing a stent 71 having struts 72 spaced apart longitudinally of the axis and between longitudinally extending circumferentially spaced apart ribs 73 as shown in FIG. 9. To accomplish this it is merely necessary to provide struts 72 at opposite ends having greater lengths than the struts therebetween to achieve flanged portions at both ends of the stent to aid in again assuring that the stent will firmly grasp the walls of the vessel in which it is placed and will be retained in that location. Such a stent can also be deployed in a conventional manner by the use of a balloon or by providing a self-expanding stent.

From the foregoing it can be seen that a new and improved stent has been provided which has a capability of expanding without shrinking. These capabilities can be incorporated into stents of various lengths and into stents which have expanded extremities. Such characteristics aid the physician in deploying such stents without danger of rupturing or damage of the balloon which is used for expanding the stent. The lack of shrinkage in length of such stents during expansion also facilitates the proper positioning of the stent in the vessel.

What is claimed:

1. A stent comprising a cylindrical member having an outside diameter, a length and having first and second ends and an intermediate portion between the first and second ends, said cylindrical member being formed of a metal and having a wall defining a central bore having a longitudinal axis extending from the proximal end to the distal end, said cylindrical member having a plurality struts extending in the wall spaced apart of the longitudinal axis and permitting radial expansion of the cylindrical member from a contracted condition to an expanded condition, means extending in the wall to prevent shrinkage in length of the cylindrical member as it is expanded from a contracted position to an expanded position, said means extending in the wall to prevent shrinkage in length of the cylindrical member as it is expanded being comprised of a plurality of longitudinally extending circumferentially spaced-apart ribs which serve as compression resisting members, each of said ribs extending the length of the cylindrical member, said plurality of struts extending circumferentially between adjacent ribs and being secured to adjacent ribs, said plurality of struts when the cylindrical member is in a contracted position having portions which are folded with respect to each other, said plurality of struts including struts adjacent the first end of the cylindrical member having lengths which are greater than the lengths of at least certain of the other struts so as to permit said first end to be flared outwardly with respect to the intermediate portion when the stent is moved from the contracted condition to an expanded condition.

2. A stent as in claim 1 wherein said plurality of struts includes struts adjacent the second end of the cylindrical member having lengths which are greater than the lengths of at least certain of the other struts exclusive of the struts at the first end so that when the cylindrical member is moved from a contracted position to the expanded position, both first and second ends of the stent are flared outwardly with respect to the intermediate portion of the cylindrical member.

* * * * *